(12) United States Patent
Gordon (10) Patent No.: US 6,803,999 B1
(45) Date of Patent: *Oct. 12, 2004

(54) ANALYTICAL DISC WITH OPTICALLY TRACKABLE ENCODED INFORMATION AND RELATED OPTICAL INSPECTION SYSTEM

(76) Inventor: John Francis Gordon, 5 Park Crescent, Torrance, Glasgow G64 4BH (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/642,996

(22) Filed: Aug. 21, 2000

Related U.S. Application Data

(63) Continuation of application No. 09/156,475, filed on Sep. 18, 1998, which is a continuation of application No. 08/809,402, filed as application No. PCT/GB95/02186 on Sep. 15, 1995, now Pat. No. 5,892,577.

(30) Foreign Application Priority Data

Sep. 21, 1994 (GB) .............................................. 9418981

(51) Int. Cl.⁷ ......................... G01N 21/03; G01N 21/29
(52) U.S. Cl. ...................... 356/73; 356/436; 422/82.05; 422/82.09
(58) Field of Search ................... 356/72, 436; 436/164, 436/165; 422/82.05, 82.09

(56) References Cited

FOREIGN PATENT DOCUMENTS

EP           417305 A   *   9/1990

* cited by examiner

Primary Examiner—Zandra V. Smith (57) ABSTRACT

A disc and analytical system for optical inspection of biological, chemical or biochemical samples located on or in the disc. Encoded information is arranged on or in the disc for optical tracking and scanning by the optical inspection system.

25 Claims, 6 Drawing Sheets

ANALYTICAL DISC WITH OPTICALLY TRACKABLE ENCODED INFORMATION AND RELATED OPTICAL INSPECTION SYSTEM

This application is a continuation of copending application Ser. No. 09/156,475, filed on Sep. 18, 1998; which is a continuation of application Ser. No. 08/809,402, filed on Jul. 28, 1997, which is now U.S. Pat. No. 5,892,577, issued on Apr. 6, 1999; which is a 371 of PCT/GB95/02186, filed Sep. 15, 1995; which claims priority from UK Patent Application No. 9418981.8 filed Sep. 21, 1994.

BACKGROUND OF THE INVENTION

The present invention relates to apparatus and to a method for carrying out optical analysis of samples and is applicable in particular to the analysis of biological, chemical and biochemical samples.

Many chemical, biochemical and biological assays rely upon inducing a change in the optical properties of a biological sample being tested. For example, in order to test for the presence of an antibody in a blood sample, possibly indicating a viral infection, an enzyme-linked immunosorbent assay (ELISA) can be carried out which produces a visible coloured deposit if the antibody is present. An ELISA makes use of a surface which is coated with an antigen specific to the antibody to be tested for. Upon exposure of the surface to the blood sample, antibodies in the sample bind to the antigens. Subsequent staining of the surface with specific enzyme-conjugated antibodies and reaction of the enzyme with a substrate produces a precipitate which shows up the level of antigen binding and hence allows the presence of antibodies in the sample to be identified. This identification is usually carried out using a light microscope which allows an area of the substrate to be viewed by an operator.

In addition to colour staining using an ELISA, techniques such as fluorescence and gold labelling can be used to alter the optical properties of biological antigen material. Similar techniques are also used in general histology to visualise specific areas of tissue, e.g. particular cell types or cell structures, as well as in cell culture.

A significant disadvantage of existing optical analysis techniques is that they are open to human error because of their subjective nature. These techniques are also not suited to uses where a high throughput of samples is required, for example in blood screening applications or cervical smear tests, and are thus relatively expensive to use. The cost factor is exacerbated because, more often than not, different equipment is required for each particular technique.

An object of the present invention is to provide a technique for carrying out the optical analysis of samples which overcomes or at least mitigates certain of these disadvantages.

It is also an object of the present invention to provide an optical analysis technique which allows high speed automatic analysis of biological, biochemical and chemical samples and which is versatile enough to allow it to be used for a variety of different studies.

These objects are achieved by adapting the technology which has been developed in the field of audio and video compact discs to scan surfaces, to which a sample has been attached, using a light beam which is substantially focused onto that surface. A detector is arranged to detect light reflected from, or transmitted through that surface, and to determine from analysis of the detected light whether the light beam has been interfered with by the sample material.

According to a first aspect of the present invention there is provided a method of conducting an optical inspection of a biological, chemical, or biochemical sample, the method comprising the steps of:

supporting the sample on a substrate; directing a beam of electromagnetic radiation from a radiation source onto the substrate;

scanning the beam over the substrate by rotating the substrate about an axis substantially perpendicular to the substrate and by moving the radiation source in a direction having a component radial to said axis; and detecting radiation reflected from and/or transmitted through the substrate and sample and providing an output signal corresponding to the detected radiation.

According to a second aspect of the present invention there is provided a system for automatically carrying out an optical inspection of a sample to determine whether or not the sample comprises material which interferes with incident electromagnetic radiation, the system comprising:

a substrate having a surface for supporting the sample;

a source of electromagnetic radiation for providing a beam of electromagnetic radiation;

means for scanning said beam across said surface of the substrate; and detector means which in use is arranged to detect electromagnetic radiation reflected from and/or passing through the substrate and the sample, the substrate being provided with distributed electromagnetic radiation modulating means for modulating at least a part of said beam with a digitally encoded position address indicative of the location on said surface on which the beam is currently directed, the detector means being arranged to decode the modulated electromagnetic radiation beam to determine the encoded address and to determine if the received beam has been modulated by any of said material which may be present in the sample.

The present invention enables the rapid scanning of a surface coated with components from a sample to determine their presence and also if necessary their optical properties. The system is particularly suited for carrying out the automatic inspection of samples with a high throughput. Moreover, provision of address information in or on the substrate enables the precise position of the electromagnetic radiation beam on the surface to be determined which in turn allows the accurate mapping of optical data, corresponding to attached material, to the surface. This enables regions of interest on the surface to be easily and quickly relocated.

The present invention is suited to carrying out ELISA where the specific antigen is coated onto the surface of the substrate. The surface is then exposed to the analyte and subsequently the specific enzyme and the resulting sample scanned to detect and quantify the enzyme linked to the surface. The system is also suited to carrying out histological analysis and to the quantitative study of gels run using electrophoresis.

Preferably, the electromagnetic radiation is light, e.g. infra-red, visible or ultra-violet.

According to a third aspect of the present invention there is provided a system for automatically carrying out an optical inspection of a sample to determine whether or not the sample comprises material which interferes with incident electromagnetic radiation, the system comprising:

a substantially planar substrate having a surface for supporting the sample;

a source of electromagnetic radiation for providing, a beam of electromagnetic radiation;

means arranged on one side of the substrate for scanning the beam across the surface of the substrate;

a first detector for detecting electromagnetic radiation reflected from the substrate and the sample;

a second detector for detecting electromagnetic radiation passing through the substrate and the sample; and control means coupled to the first and second detectors and for causing said beam to scan the surface of the substrate in dependence upon one or both of the outputs of the detectors and for detecting the presence of said components.

In a preferred embodiment of the above second aspect of the present invention the control means is arranged to determine the difference between output signals provided by said first and second detectors, which are representative of the signals detected, for the purpose of detecting said material without signal artifacts arising from, for example, dirt present on the side of the substrate opposite the support surface. The substrate may be provided with distributed address means for modulating the light beam with digitally encoded position information indicative of the area currently being scanned by the light beam, one or other of the detectors being arranged to decode the received light signal to determine the address of the location on which the light beam is incident.

According to a fourth aspect of the present invention there is provided a system for automatically carrying out an optical inspection of a sample to determine whether or not the sample comprises material which interferes with incident electromagnetic radiation, the system comprising:

a disc comprising a plastic base layer on the upper surface of which is formed a plurality of perturbations, for interfering with incident electromagnetic radiation, representing digitally encoded data, and a surface for supporting the sample;

disc reading apparatus including a source of electromagnetic radiation for providing a beam of electromagnetic radiation, scanning means for scanning the beam across the upper surface of the disk, and an electromagnetic radiation detector for detecting radiation reflected from and/or transmitted through the disk and said sample components; and means for rotating the disc about an axis substantially perpendicular to said beam, wherein, in addition to being modulated by information digitally encoded onto the disc, the beam is additionally modulated by any of said material which is attached to the support surface of the disc.

Preferably, said electromagnetic radiation is visible light although infra-red or ultra-violet radiation may be suitable.

Preferably, the disc comprises a lower layer of transparent plastic on the surface of which is impressed, or otherwise produced, said digital information. This surface is coated with a partially reflective layer, for example of aluminium, which in turn may be covered by a further layer of transparent plastic.

In an embodiment of the above fourth aspect of the invention the upper surface of the disc is provided with a 3D surface topology arranged to provide growth and attachment cues for cells grown on the surface. For example, the surface may be provided with a rectangular grating for causing cells to align in a chosen direction. Alternatively, growth and attachment cues may be provided by chemical patterning of the surface, e.g. using fibrenectin, produced, for example, using photolithography.

In another embodiment of the above fourth aspect of the present invention the upper surface of the disc is coated with a gel suitable for carrying out electrophoresis on proteins, DNA etc. In order to run the gels radially, a first electrode may be provided at the centre of the disc with a second electrode being provided around the periphery of the disc. A well may be formed in the gel into which the analyte can be placed.

In order to calibrate a system embodying the present invention, the disc may be provided with a calibration track, e.g. a series of 256 grey levels. These levels may be printed onto the surface of the track using an ink jet printer.

According to a fifth aspect of the present invention there is provided a substrate for use in a system which is arranged to carry out an optical inspection on the substrate to determine whether or not material which interferes with incident electromagnetic radiation is present on a surface of the substrate, the substrate including a preformed calibration scale which enables calibration of said system.

Preferably, the calibration scale is a series of graded grey regions which reflect or transmit light to varying degrees. This scale may be printed on a surface of the substrate using an ink jet printer.

According to a sixth aspect of the present invention there is provided apparatus for conducting an optical inspection of a biological, chemical, or biochemical sample supported on a substrate, the apparatus comprising;

means for supporting a substrate and for rotating the substrate about an axis substantially perpendicular to the substrate;

a source of electromagnetic radiation for providing a beam of electromagnetic radiation;

drive means for moving the radiation source over the mounted sample in a direction having a component radial to said axis so that in combination with the means for rotating the substrate the radiation beam can be scanned over the substrate; and detector means for detecting radiation reflected from or transmitted through the substrate and sample and for providing an output signal corresponding to the detected radiation.

For a better understanding the present invention and in order to show how the same may be carried into effect embodiments of the invention will now be described, by way of example, with reference to the accompanying drawings, in which:

FIGS. 4 (A) to (C) illustrate graphs of outputs from detectors D1 and D2 shown in FIG. 3;

Figure 1:
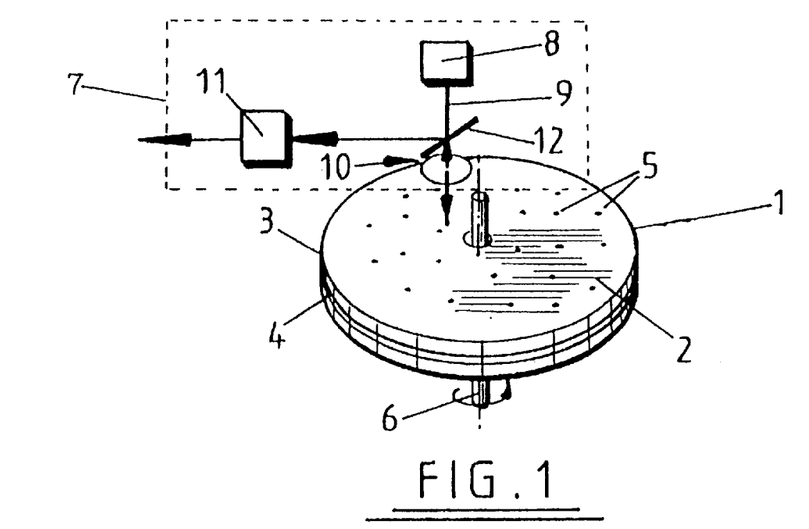
FIG. 1 shows a diagrammatic view of a first embodiment of the present invention.

As discussed above, it is desirable to be able to optically scan a surface to which material is attached for the purpose of quantitative analysis of the material, or of a sample from which the material is derived or extracted. FIG. 1 illustrates in simplified form a system which enables this to be achieved. The system uses a circular disc 1 (although any other suitable shape of disc may be used) which comprises lower and upper layers of transparent plastic material 2,3 which provide the disc with smooth upper and lower surfaces. Sandwiched between the two plastic layers is a thin layer of metal 4 which provides a light reflecting surface. The plastic may be of any suitable material such that the material to be optically analysed can be attached to the upper surface of the disc in the same way in which it would be attached to any conventional substrate.

It the system is used to carry out an ELISA, the appropriate antibody is bound to the upper surface of the disc (this may require some pre-preparation of the surface). The surface is then exposed to the sample to be tested, e.g. blood plasma, in order to bind any antigens in the sample to the antibodies. The surface is then washed to remove any excess, unbound, material and exposed to the appropriate enzyme-conjugated antibodies 5 which attach to the bound antibodies. The bound enzymes 5 can be visualised by reacting them with a substrate to produce a coloured precipitate. The precipitate presents a multiplicity of minute opaque patches over the upper surface of the disc. It will be apparent that the system is equally applicable to other types of assay which produce a colour, or other light interfering, change.

The disc is mounted on a rotatable shaft 6 which is driven by a drive means (not shown in FIG. 1) causing the disc to rotate. An optical block 7 is mounted above the disc and is movable along a substantially linear track. The optical block 7 comprises a laser diode 8 which produces a beam of coherent light 9 which is collimated and focused on to the surface of the disc 1 by a lens arrangement 10. The optical block also comprises a detector 11 for detecting light reflected from the surface of the metal layer within the disc. The lens arrangement 10 includes a polarising prism 12 which allows only vertically polarised light to pass therethrough and a quarter wave plate 37 which causes light to be rotated by 45°.

In operation, the disc is rotated by the drive means relative to the optical block. With the block stationary the light beam produced by the laser diode travels around a circular track of the disc. By moving the optical block along its linear track it is possible to scan the laser beam around any selected circular track of the disc. In areas of the disc surface where no light absorbing material is present, light passes through the upper plastic layer, is reflected from the metal layer, and travels back to the optical block, through the upper plastic layer. Light entering the optical block encounters first the quarter wavelength plat 37, which rotates the light by a further 45°, and then the polarising prism which, because the polarization of the reflected light has been rotated by 180°, causes the light to be redirected at right angles towards the detector.

When the light beam is incident upon areas of the disc surface where light absorbing material is present, light is absorbed by the material, both upon entry to and exit from the upper plastic layer of the disc, and the light received by the detector 11 is substantially reduced.

The detector 11 is coupled to a data analysis and logging system which stores the output of the detector. This system may store the output as a continuous analogue signal or as discrete digital samples which represents a reduced resolution image of the surface. Assuming the latter, the sampling rate may be varied to fit the data storage capacity available.

The optical, mechanical and electrical means so far described for implementing an analyte detector are substantially as conventionally used for reading data from compact discs. One such conventional system is described in the text book 'Digital, Audio and Compact Disc Technology', 2nd edition, Edited by Luc Baert et al (Sony Service Centre Europe), *Newnes*, 1994.

The system of FIG. 1 is adequate for obtaining an image of the disc surface, or a portion of that surface when the actual location of the portion itself is no significance. However, it may be desirable to be able to scan a selected area of the disc surface, for example where an ELISA has been carried out only in that region, or when it is desired to look again at a specific region of interest.

Figure 2:
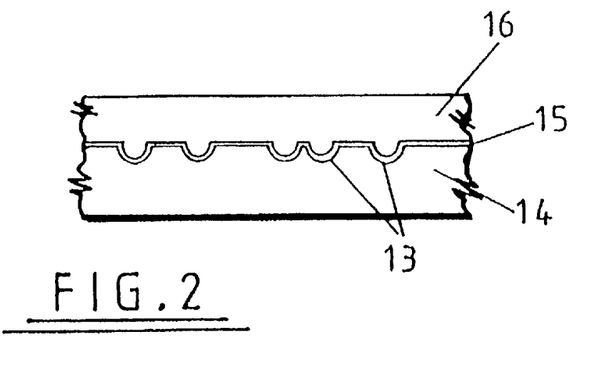
FIG. 2 shows a cross-sectional view of a part of a disc for use with the embodiment of FIG. 1, drawn to a larger scale.

Conventional compact discs encode digital information in an intermediate region of the disc by producing a series of perturbations 13 (e.g. bumps or pits) on the upper surface of a lower plastic layer 14 and subsequently coating this surface with a reflective layer 15 such as a thin layer of aluminium. The reflective layer is then covered with a layer of transparent plastic 16 which provides protection for the intermediate layer (FIG. 2).

It is possible to use this same technique to digitally encode position information into the disc of FIG. 1. Assuming that the position origin is at the centre of the disc, the first position on the innermost circular track or spiral can be imprinted with the position code zero (in binary representation). Position codes can be imprinted at discrete positions (e.g. every 2 to 3 $\mu$m or at any other appropriate interval) around that innermost track incrementing by one between each position. Similarly, the codes are incremented from track to track. Alternatively, address information may be distributed according to a track/sector arrangement in the same way in which servo-codes are encoded onto magnetic floppy and hard disks.

Over areas of the surface of the disc which are not covered by opaque material, light incident on the upper surface of the disc is transmitted through the upper transparent plastic protective layer and is incident upon the reflective layer. This light is reflected from the reflective metal coating except where that coating lies over a bump which causes incident light to be dispersed and not directly reflected back to the detector. The output from the detector can therefore be demodulated to determine the address of the disc surface which is currently being scanned.

Over areas of the disc surface where opaque material causes the incident light beam to be substantially absorbed rather than reflected, no position information will be present at the output of the detector. However, if the density of the opaque material is relatively low the gaps in the address information may not be significant.

Figure 3:
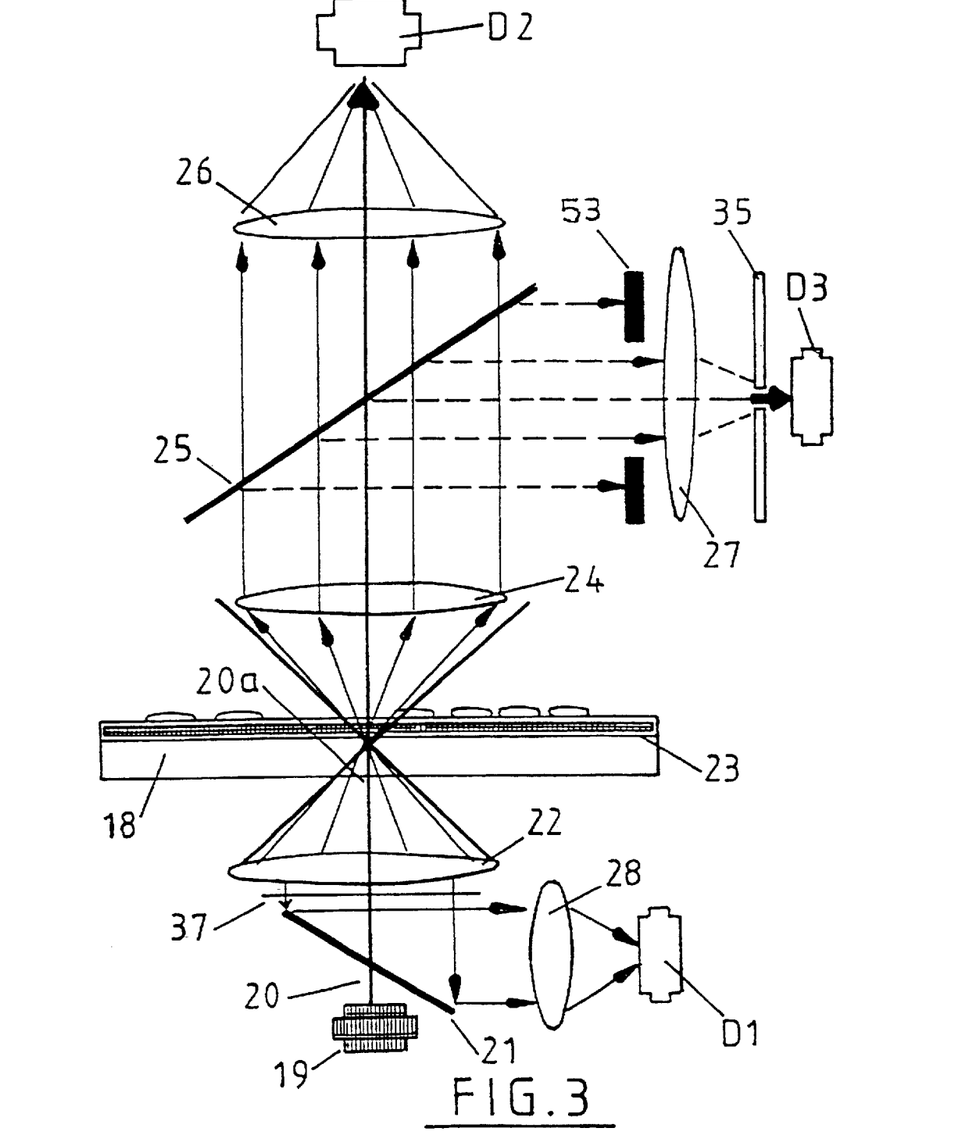
FIG. 3 shows a detailed diagrammatic side elevational view of a second embodiment of the present invention.

In situations where address information is more critical however, a more sophisticated system can be utilised for which the optics are shown in FIG. 3 and which makes use of discs having address information digitally encoded and distributed over an intermediate layer as described above. This system also makes use of the fact that the reflective layer can be made to transmit a significant proportion of the incident light (e.g. 40%). As with the system of FIG. 1, the system of the second embodiment includes a shaft 17 on which the disc 18 is mounted and which causes the disc to rotate and means for moving the optics along a linear track relative to the upper surface of the disc. The rotation and displacement means are not shown in FIG. 2 for simplicity.

The optical system of FIG. 3 comprises a light source 19, which may be for example a semi-conductor laser or a light emitting diode, arranged beneath the disc. The output beam 20 of the light source is directed to an optical axis 20a to a polarising prism (a beam splitter) 21 which allows only light of a given polarisation to pass, i.e. only the light received directly from the laser. The transmitted light is then incident upon a first lens 22 which is arranged to focus light onto the lower surface 23 of the reflective layer within the disc. A fraction of the light incident upon the compact disc is transmitted through the reflective layer and exits from the upper surface of the disc. Any material attached to the upper surface will interfere with light exiting the disc.

Transmitted light which is not interfered with is received by a collimation lens 24, focused onto the upper surface of the disc, which directs the received light onto a partially transparent mirror 25 which in turn allows a fraction of the incident light to pass therethrough whilst causing the remainder to be reflected at right angles. Light passing directly through the partially transparent mirror is incident upon a further lens 26 which focuses the light onto the detection surface of a detector D2. Light reflected at right angles by the mirror 25 is incident upon a lens 27 which focuses light onto a detector D3.

As already described, a fraction of the light incident on the reflective layer within the disc is reflected back towards the first lens 22 which acts as a collimation lens directing light back to the polarising prism 21. The reflected light is now horizontally polarised and is reflected from the polarising prism at right angles to the optical axis. This reflected light is received by a fourth lens 28 which focuses received light onto a detector D1.

Light reflected by the reflective layer will be modulated with the information digitally encoded into the disc so that the output from the detector D1 will be similarly modulated. As this light does not exit from the upper surface of the disc it will not be interfered with by material attached to the upper sample support surface of the disc and address information can be determined from the output of D1 with minimal error.

Although not shown in FIG. 3 the optical block situated below the disc also incorporates tracking optics which enables the correct tracking of the disc tracks in a similar way to that used in conventional compact disc players. The tracking optics comprise a diffraction grating, located in this embodiment at plane 37 in FIG. 3, which splits the output from the laser into three parallel beams which are subsequently focused by the first lens to provide three slightly spaced-apart spots. The spacing between these spots is such that when the central spot is directly over the centre of one track the other two spots lie on either side of that track. The detector D1 actually comprises three adjacent detectors which receive reflected light and the spacing of which is equivalent to that between the beam spots. In order to align the laser correctly, the laser position is adjusted until the output from the centre detector is maximum and the outputs from the two side detectors is a minimum. A feedback control system is used to maintain the correct tracking.

The output provided by detector D2 is modulated with the digital address information encoded onto the disc and, provided that no light absorbing material is attached to the upper surface of the disc, is substantially of the form of the output of detector D1, i.e. the ratio of the output signals of D1 and D2 will be constant. However, if light absorbing material is present on the upper surface of the disc this will interfere with light transmitted through the reflective layer and the output from detector D2 will drop whilst that from D1 will remain constant. The ratio of the output signals of D1 and D2 will change, accordingly. If the material attached to the surface of the disc is reflective, e.g. gold labelled, the output of D1 will rise whilst that of D2 will fall when the light beam scans the material. The ratio of D1 to D2 will indicate the presence of such material.

Figure 4:
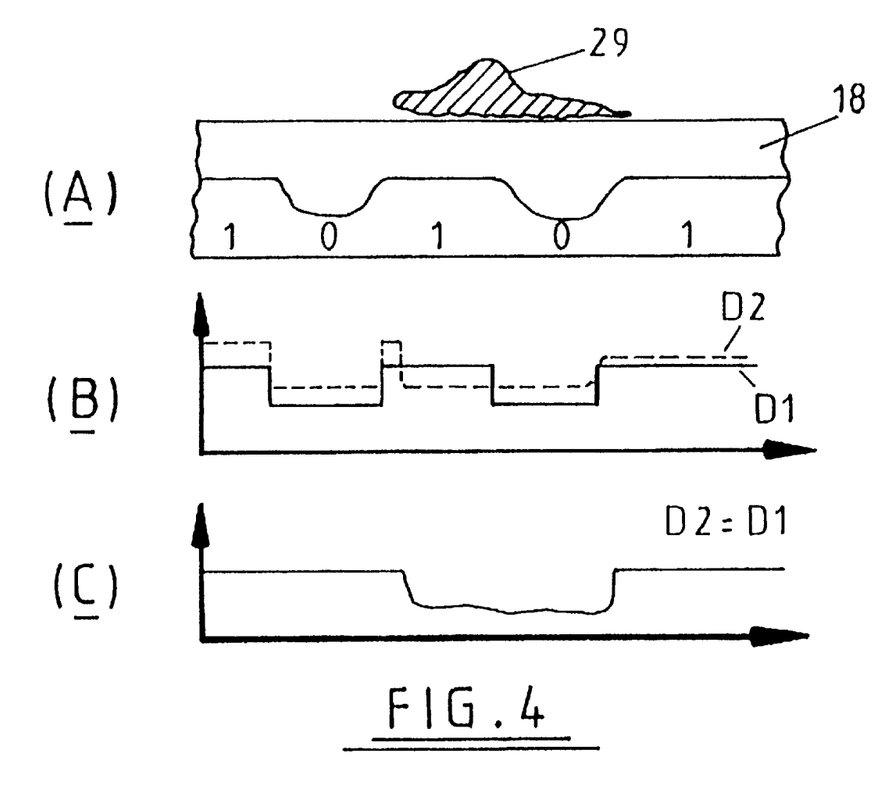

FIG. 4 illustrates the case where the bound material is absorbent but not reflective and shows at (A) a cross-section taken through typical disc to the surface of which a stained cell 29 is attached. The reflective layer beneath the support surface is encoded with the digital address 10101. As the beam scans along the track the ratio between the output signals of detectors D1 and D2 (FIG. 4B) remains constant where the upper surface is not covered by the cell. In the central area, however, where the cell is shown covering the upper surface, the signal produced by detector D2 falls so that the ratio (FIG. 4C) of the signals produced by D1 and D2 similarly drops.

Figure 5:
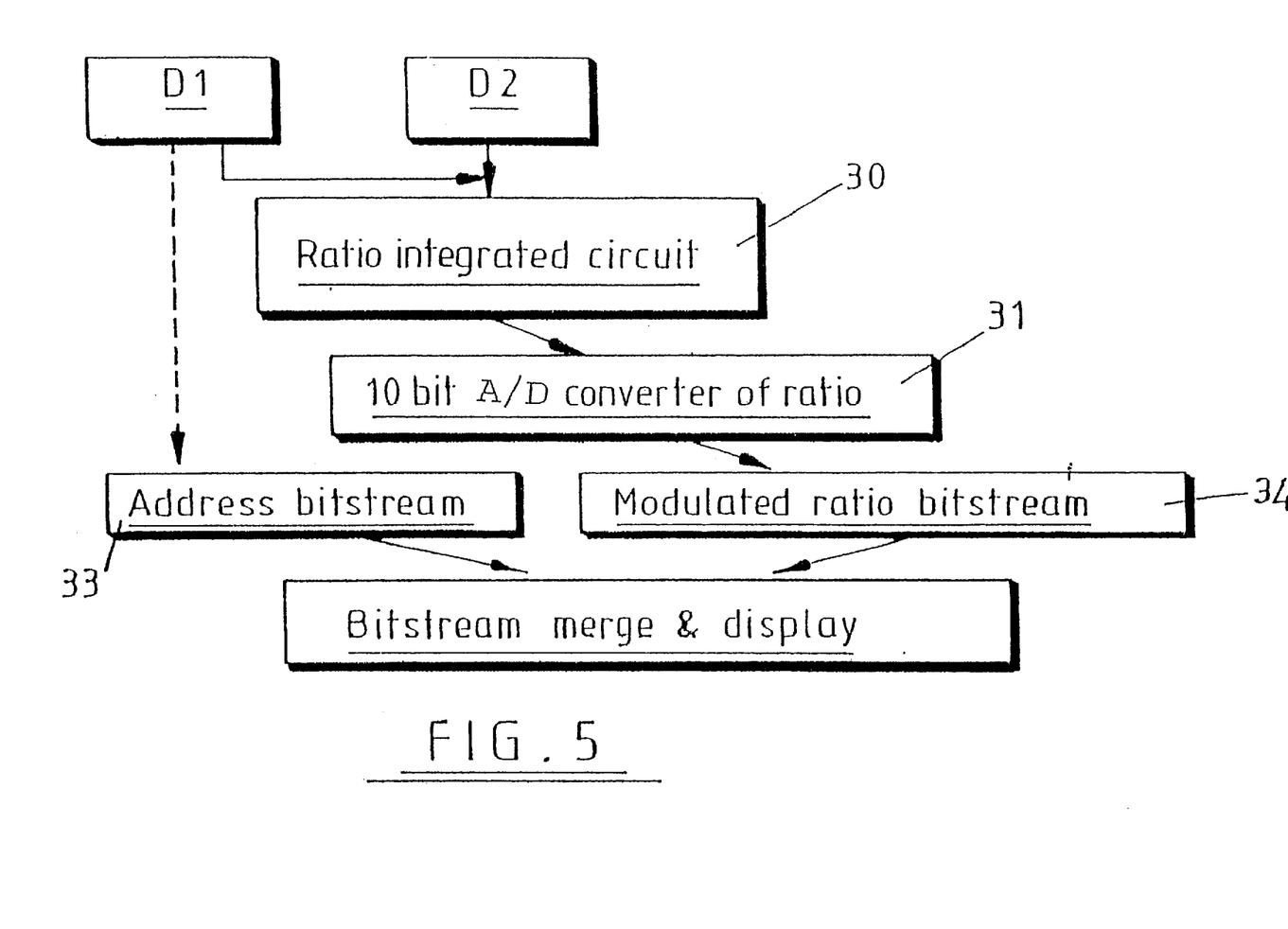
FIG. 5 shows a schematic diagram of a control system of the embodiment of FIG. 4.

FIG. 5 shows a block diagram of a system for controlling the embodiment of FIG. 3 with the flow of data through the system being indicated by arrows. The analogue outputs from detectors D1 and D2 are received by an integrated circuit 30 which determines the ratio of the two outputs. This ratio is then converted to digital form by an analogue to digital converter 31 and transmitted to a bitstream generator 34 for compression using bitstream modulation. The output from detector D1, which represents the digitally encoded address information, is also transmitted to an address bitstream generator 33 for compression. The two channel bitstream data is received by a bitstream merge and display unit which processes the data for storage and for display.

In order to provide more stringent measure of the variations in the intensity of light transmitted through the disc the detector D3 is provided (although this is optional) which receives light from the partially transparent mirror through the aperture 53, lens 27 and pinhole arrangement 35. This arrangement effectively reduced the area of the disc surface from which light is received by the detector D3 and also reduces the depth of focus. If the output of detector D2, or the ratio D1:D2, exceeds a predetermined threshold the output of detector D3 can be used to increase the resolution with which the surface of the disc is viewed. The use of detectors D2 and D3 in combination prevents the likelihood of the detector D2 producing errors if the system used only detector D2. D3 may alternatively provide a second type of detector for detecting for example fluorescent light emitted by material attached to the surface of the disc.

Figure 6:
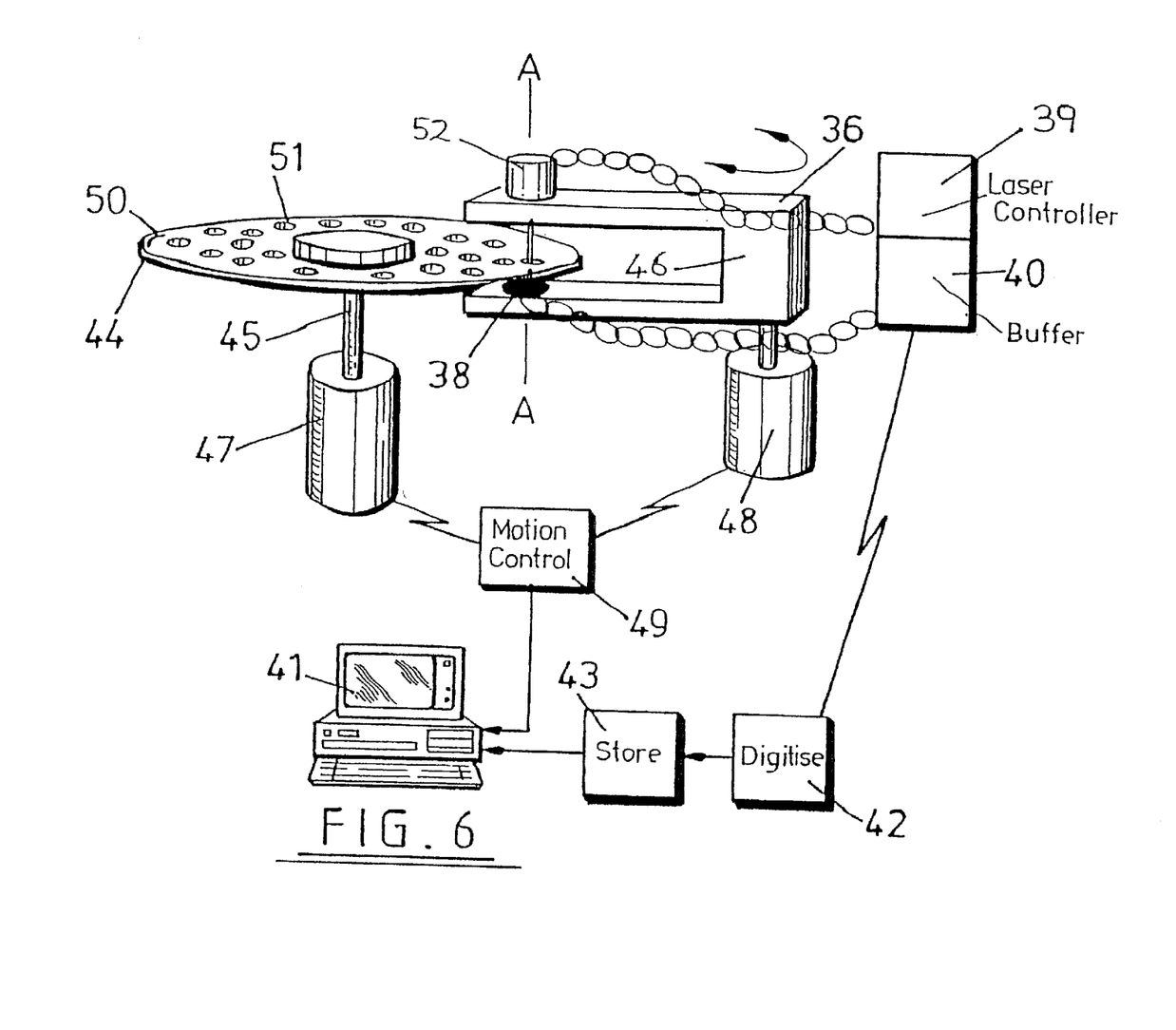
FIG. 6 shows a diagrammatic view of a third embodiment of the invention.

FIG. 6 shows a further embodiment of the invention in which absolute position information can be determined, although the accuracy of this information may be somewhat less than that provided by the embodiment of FIGS. 4 and 5. However, the disc construction is considerably simplified.

The optical inspection system has a 'U' shaped arm 36 with a light source 52 and a detector 38 attached to the upper and lower ends of the arm respectively. The source and detector are connected to a laser controller 39 and a buffer 40, the latter being arranged to transfer detected signal data to a personal computer 41 via an analogue to digital converter 42 and a data store 43.

The disc 44 upon which the sample to be inspected is attached or supported is mounted on a rotatable spindle 45 which lies parallel to the bight 46 of the arm 36. The spindle 45 is driven be a spindle motor 47. The optical axes of the light source 37 and detector 38 are aligned with one another along the axis A—A.

The arm 36 is coupled to a stepper motor 48 which precisely rotates the arm in a plane parallel to the plane of the disc 44 such that, in combination, rotation of the arm and of the disc allows the light source/detector arrangement to be scanned across the entire useable surface of the disc. The stepper motor 48 is controlled by a motion controller 49, which in turn is controlled by the computer 41, such that the relative position of the spindle 45 can be determined to within an accuracy of 6 $\mu$m.

The disc is of a completely transparent material but is provided with a black bar 50 around a portion of its upper peripheral surface. The bar 50 acts as an angular calibration marking for the inspection system. When it is required to inspect a disc, the arm 36 is moved to an outermost "home" position, where the light source/detector arrangement is situated off the disc 44. In this position, the laser and detector are calibrated to ensure a constant, maximum, output signal. The arm 36 is then rotated to move the light source/detector arrangement towards the disc.

When the edge of the disc is detected, the arts is held stationary until the calibration marking 50 interrupts the beam. The leading edge of the marking 50 provides an origin to which the angular position of the detector can be referenced whilst the edge of the disc provides an origin for the radial position. Due to the accuracy of the stepper motor 48 and the spindle motor 46, it is then possible to precisely determine the position of the light source/detector arrangement relative to the disc.

Figure 7:
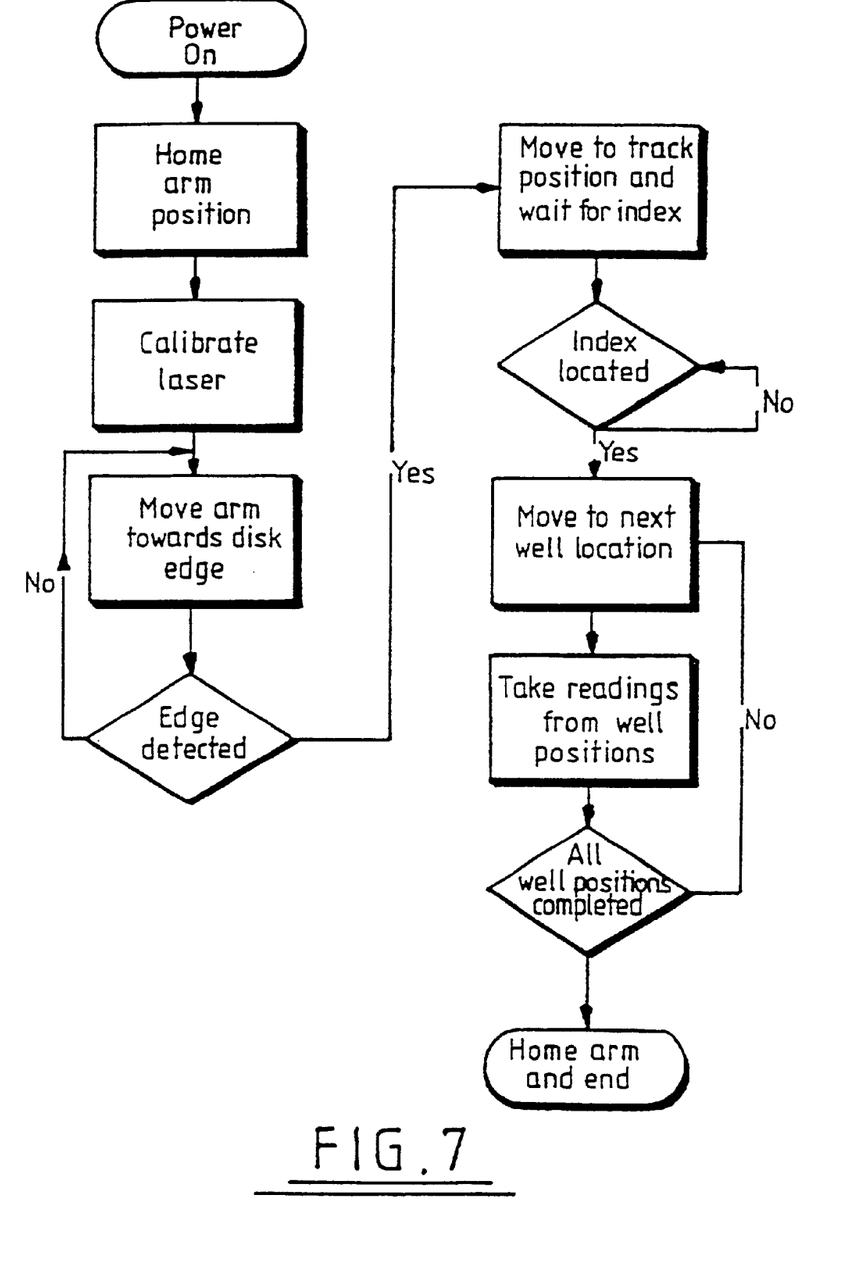
FIG. 7 shows a schematic diagram of a control system of the embodiment of FIG. 6.

In the system of FIG. 6, the disc 44 comprises a plurality of wells or indentations 51 formed in its upper surface. The wells contain the sample to be inspected and are filled, for example, by microtitration. Rather than scan the whole surface of the disc, the personal computer may be arranged to step the light source/detector arrangement over the disc surface from one well to another. This is enabled by the precise position information obtained from the calibration marking and the disc edge. FIG. 7 shows a flow diagram of the control process for this system.

The system of FIG. 6 may be modified so that the light source 37 and the detector 38 are both arranged on the same side of the disc, with the disc being provided with a reflective coating on or beneath the surface on which the sample is supported. In this arrangement the detector detects light reflected from the reflective coating. The two main advantages of the arrangement are that the surface of the disc which does not support the sample may be safely handled, as it does not lie in the light transmission path, and that the signal to noise ratio of the optical inspection process may be increased because light will have to pass through a sample twice in travelling from the source to the detector.

It will be apparent that various modifications may be made to the above described embodiments without departing from the scope of the invention. For example, the support surface of the disc may be scanned with infra-red or ultraviolet radiation rather than visible light. It is also possible to scan the surface with radiation which excites fluorescence in material attached to the surface and to use the detector (D2 or D3) arrangement to detect light at the emission wavelength.

It is also possible to construct the disc in such a way that the support surface is internal to the disc and is not the upper surface of the disc. This may provide the advantages that the sample is not damaged by handling and that a precise volume of sample may be analysed. To enable the system to be used for running gels (e.g. to identify proteins, DNA etc), an appropriate gel may be provided on the upper surface of the disc. Electrodes for applying a potential across the gel may be formed integrally therewith or may be printed, or otherwise deposited, on the upper surface. The electrodes may be spaced radially or circumferentially. Pits may be provided in the gel into which the material to be run can be placed.

Another modification to the above described embodiments involves replacing the light detector with a photodiode array, e.g. a CCD array. A preferred form of array is a linear array extending radially with respect to the disc. The light source would take the form of a laser line generator arranged to generate a radially extending line of light aligned with the diode array. Some degree of optical magnification may be incorporated between the source and the generator to allow the resolution of the system to be varied. After each rotation of the disc, the source/detector arrangement would be stepped inwardly by the length of the laser line. The advantages of this arrangement are higher speed and higher resolution.

What is claimed is:

1. A disc for use in conducting an optical inspection of a biological, chemical or biochemical sample, said disc comprising;
   a substrate having a surface including a center portion and a perimeter portion;
   optically trackable encoded information located on said surface, said encoded information being located in both said center portion and said perimeter portion of said substrate surface; and
   a sample support surface for supporting said biological, chemical or biochemical sample for optical inspection.

2. A disc according to claim 1 in which said optically trackable encoded information is in the form of a plurality of circular tracks located in said center portion and said perimeter portion of said substrate surface or, a spiral track which extends from said central portion to said perimeter portion of said substrate surface.

3. A disc according to claim 1 in which said optically trackable encoded information is in the form of a track which includes gaps in said encoded information.

4. A disc according to claim 1 in which said encoded information is reflective.

5. A disc according to claim 1 in which said encoded information is semi-reflective.

6. A disc according to claim 1 which includes a cover over the encoded information located on the surface of said substrate.

7. A disc according to claim 2 in which said disc is a compact disc.

8. A disc according to claim 1 in which said disc comprises a biological, chemical or biochemical material attached to said sample support surface.

9. A disc according to claim 8 in which said material attached to said sample support surface is colored, reflective or fluorescent.

10. A disc according to claim 1 which includes a gel and electrodes for applying a potential across said gel.

11. A system for conducting optical inspection of a biological, chemical or biochemical sample comprising:
   (A) a disc according to claim 1; and
   (B) an optical inspection system including:
      (a) a radiation source for providing at least one beam of electromagnetic radiation;
      (b) a detection system including one or more detectors for detecting radiation reflected from and/or transmitted through said disc and tracking optics which provide tracking of said beam of radiation on said optically trackable encoded information.

12. A system according to claim 10 in which said radiation source is located relative to said disc so that said sample support surface is located between said radiation source and said substrate surface.

13. A system according to claim 11 in which said radiation source is located relative to said disc so that said substrate surface is located between said radiation source and said sample support surface.

14. A system according to claim 13 in which said encoded information is semi-reflective and said detection system comprises two detectors wherein one of said two detectors is located on the same side of said disc as said radiation source and the other of said two detectors is located on the side of said disc opposite said radiation source.

15. A system according to claim 14 in which said detection system further comprises a third detector located on the side of said disc opposite said radiation source.

16. A system according to claim 11 in which said detection system comprises a video monitor for viewing the results of said optical inspection.

17. A system according to claim in 11 which said disc comprises a gel and electrodes for applying a potential across said gel.

18. A method of conducting an optical inspection of a biological, chemical or biochemical sample, said method comprising the steps of:
   providing a disc according to claim 8; and
   optically inspecting of the material attached to said sample support surface.

19. A method according to claim 18 wherein said step of optically inspecting includes:
   tracking a beam of radiation along the optically trackable encoded information to produce detectable radiation which is reflected from and/or transmitted through said optical disc; and
   measuring said detectable radiation to detect the presence of, said material on said sample support surface, in which said step of measuring said detectable radiation includes providing an optical image of said material.

20. A method according to claim 18 wherein said step of optically inspecting includes:
   tracking a beam of radiation along the optically trackable encoded information to product detectable radiation which is reflected from and/or transmitted through said optical disc; and
   measuring only said detectable radiation which is reflected from said disc detect the presence of said material on said sample support surface.

21. A method according to claim 18 wherein said step of optically inspecting includes:
   tracking a beam of radiation along the optically trackable encoded information to produce detectable radiation which is reflected from and/or transmitted through said optical disc; and
   measuring detectable radiation which is both reflected from and transmitted through said disc to detect the presence of said material on said sample support surface.

22. A method according to claim 18 in which said sample support surface is internal to said disc.

23. A method according to claim 18 wherein said step of optically inspecting includes:
   tracking a beam of radiation along the optically trackable encoded information to produce detectable radiation which is reflected from and/or transmitted through said optical disc; and
   measuring said detectable radiation to detect the presence of said material on said sample support surface.

24. The system according to any one of claims 11–19 wherein said optical inspection system includes a quarter wave plate through which said beam of radiation is passed.

25. The method of any one of claims 18–23 wherein said step of measuring includes passing said beam of radiation through a quarter wave plate.

* * * * *